(12) United States Patent
Chen et al.

(10) Patent No.: US 12,117,445 B2
(45) Date of Patent: Oct. 15, 2024

(54) HIGH THROUGHPUT AFFINITY SAMPLE PREPARATION FOR MYCOTOXIN ANALYSIS

(71) Applicant: Waters Technologies Corporation, Milford, MA (US)

(72) Inventors: Lingyun Chen, Westborough, MA (US); Jianmin Liu, Northborough, MA (US)

(73) Assignee: Waters Technologies Corporation, Milford, MA (US)

( * ) Notice: Subject to any disclaimer, the term of this patent is extended or adjusted under 35 U.S.C. 154(b) by 404 days.

(21) Appl. No.: 17/203,920

(22) Filed: Mar. 17, 2021

(65) Prior Publication Data

US 2021/0293813 A1   Sep. 23, 2021

Related U.S. Application Data

(60) Provisional application No. 62/991,141, filed on Mar. 18, 2020.

(51) Int. Cl.
   *G01N 33/569* (2006.01)
   *G01N 21/77* (2006.01)
   *G01N 33/531* (2006.01)
   *G01N 33/577* (2006.01)

(52) U.S. Cl.
   CPC ..... *G01N 33/56961* (2013.01); *G01N 33/531* (2013.01); *G01N 33/577* (2013.01); *G01N 2021/7786* (2013.01); *G01N 2333/37* (2013.01)

(58) Field of Classification Search
   None
   See application file for complete search history.

(56) References Cited

U.S. PATENT DOCUMENTS

| 2008/0014582 A1 | 1/2008 | Hooper |
| 2010/0075322 A1 | 3/2010 | Hooper |

FOREIGN PATENT DOCUMENTS

| EP | 2090590 A1 | 8/2009 |

OTHER PUBLICATIONS

Huybrecht et al. Arch. Toxicol. 89: 1993-2005, 2015.*
Hu et al. Anal. Bioanal. Chem. 408: 6027-6036, 2016.*
CapturemTM. Protein A 96-Well Plate Protocol-At-A-Glance (120519), Takara Bio USA, Inc, pp. 1-4, 2018.*
Takino et al. Agilent Technologies, pp. 1-8, 2008.*
Leszczynska et al. Czech J. Food Sci. 19: 8-12, Feb. 2018.*
Thermo Scientific Pierce Assay Development Technical Handbook, Thermo Scientific, Version 2, pp. 1-74, 2011.*
Lv et al. Eur. J. Mass Spectrom. 26: 63-67, Jul. 29, 2019.*
Beloglazova et al. "Quantum dot based rapid tests for zearalenone detection." Anal. Bioanal. Chem. 403(2010): 3013-3024.
De Girolamo et al. "Analytical performances of a DNA-ligand system using time-resolved fluorescence for the determination of ochratoxin A in wheat." Anal. Bioanal. Chem. 403(2012): 2627-2634.
Hyland et al. "A Radiometric Assay for HIV-1 Protease." Anal. Biochem. 188(1990): 408-415.
International Search Report and Written Opinion issued in International Patent Application No. PCT/IB2021/052236 dated May 21, 2021.
O'Riordan et al. "Comparison of analytical methods for aflatoxin determination in commercial chilli spice preparations and subsequent development of an improved method." Food Control. 20(2009): 700-705.
Pidenko et al. "Imprinted proteins as a receptor for detection of zearalenone." Anal. Chim. Acta. 1040(2018): 99-104.
Pittet et al. "Modern methods and trends in mycotoxin analysis." Mitteilungen aud Lebensmitteleuntersuchung und Hygiene. 96.6(2005): 424-444.
Shahani et al. "Purification of MINUS: A negative regulator of microtubule nucleation in a variety of organisms." Int. J. Biol. Macromol. 39(2006): 15-22.
Sidhu et al. "Occurrence of aflatoxins in mahua (*Madhuca indica* Gmel.) seeds: Synergistic effect of plant extracts on inhibition of Aspergillus flavus growth and aflatoxin production." Food Chem. Toxicol. 47(2009): 774-777.
Zeng et al. "Recombinant antibodies and their use in biosensors." Anal. Bioanal. Chem. 402(2012): 3027-3038.

\* cited by examiner

*Primary Examiner* — S. Devi
(74) *Attorney, Agent, or Firm* — WOMBLE BOND DICKINSON (US) LLP; Deborah M. Vernon; Mark R. Deluca

(57) ABSTRACT

The present disclosure relates to a method of separating a sample including a mycotoxin. The method includes flowing the sample through a column to load the sample on the column, washing the column to reduce impurities, eluting the mycotoxin from the column, collecting an eluted sample with the mycotoxin in a sample plate, sealing the eluted sample in the sample plate, transferring the sealed sample plate, removing the eluted sample from the transferred sample plate; and analyzing the removed eluted sample. The column can include an affinity resin, such as, for example, an immunoaffinity resin. The sample plate can be a 96-well plate.

26 Claims, 2 Drawing Sheets

202 — Loading a sample with mycotoxins in a column

204 — Washing the column to reduce impurities

206 — Eluting the mycotoxin through a column

208 — Collecting the eluted sample

210 — Sealing the eluted sample

212 — Transferring the eluted sample

214 — Analyzing the eluted sample

*Fig. 2*

HIGH THROUGHPUT AFFINITY SAMPLE PREPARATION FOR MYCOTOXIN ANALYSIS

CROSS-REFERENCE TO RELATED APPLICATIONS

This application claims the benefit of and priority to the U.S. Provisional Patent Application No. 62/991,141 filed on Mar. 18, 2020, and entitled "High Throughput Affinity Sample Preparation for Mycotoxin Analysis." The contents of which are incorporated herein by reference in its entirety.

FIELD OF THE TECHNOLOGY

The present disclosure relates to isolating mycotoxins. More specifically, the present disclosure relates to high throughput immunoaffinity sample preparation for mycotoxin analysis.

BACKGROUND

Chromatography is a set of techniques for separating a mixture into its constituents. Immunoaffinity chromatography (IAC) combines the use of liquid chromatography (LC) with the specific binding of antibodies or related agents.

SUMMARY

IAC can be used in assays for a particular target or for purification and/or concentration of analytes. In some examples, purification and/or concentration occurs prior to examination by another technique. The present disclosure relates to IACs (and other affinity based chromatography) in sample preparation for mycotoxin analysis. Mycotoxin diagnostics range from rapid tests to complicated instrumental tests. Rapid tests include enzyme-linked immunosorbent assay (ELISA), lateral flow strips, and fluorometer tests, which are used as screening tests in the field. High performance liquid chromatography (HPLC) and liquid chromatography-mass spectrometry (LC/MS) methods are employed in well-established labs and can produce more accurate and confirmatory results than ELISA and other rapid tests. ELISA has been the only high throughput method that can process hundreds of samples in a few hours.

The present disclosure of a high throughput affinity sample preparation for mycotoxin analysis provides the performance of instrumental analysis such as ultra-high performance liquid chromatography (UHPLC)/MS, HPLC/MS, or LC/MS as well as the high throughput feature of a method such as ELISA. Some of the benefits of IAC high throughput solution include the ability to compete with the number of samples ELISA can process in a given time, less turnaround time (as compared to fluorometer) or hands-on time (as compared to UHPLC/MS, HPLC/MS, or LC/MS), and inexpensive consumables used in the process. In general, ELISA processes take hours (1, 2, or more hours) to run samples, whereas the present technology can process up to 96 samples within 30 minutes or less. The IAC high throughput solution also provides superior results including better coefficient of variation (CV), confirmatory results instead of screening results that lack detailed information and sufficient accuracy, multiplexing—the ability to process multiple samples at the same time, and information about subtypes including the distribution of mycotoxins). For example, with high throughput immunoaffinity sample preparation for mycotoxin analysis, the distribution of mycotoxins can be detected, e.g., the distribution of aflatoxin B1, B2, G1, G2, M1 and M2.

In one aspect, the present disclosure provides for a method of analyzing a sample comprising a mycotoxin. The method can include loading the sample in a column, wherein the column comprises an affinity resin (e.g., immunoaffinity resin); washing the column to reduce impurities (optional); eluting the mycotoxin from the column; collecting an eluted sample comprising the mycotoxin in a multi-well sample plate (e.g., a 48-sample well plate, a 96-well sample plate, etc.); sealing the eluted sample in the multi-well sample plate; transferring the sealed multi-well sample plate; removing the eluted sample from the transferred multi-well sample plate; and analyzing (e.g., analyzing with UHPLC/MS, HPLC/MS, LC/MS or a fluorescence microplate reader) the removed eluted sample.

In another aspect, the present disclosure provides for a method of separating a sample comprising a mycotoxin. The method includes loading the sample on a column, wherein the column comprises an affinity resin (e.g., immunoaffinity resin); eluting the mycotoxin from the column; collecting an eluted sample comprising the mycotoxin in a sample plate, wherein the sample plate is a 96-well plate; sealing the eluted sample in the sample plate; transferring the eluted sample in the sealed sample plate; and analyzing the eluted sample in the 96-well plate format using UHPLC/MS, HPLC/MS, LC/MS, or a fluorescence microplate reader.

In another aspect, a method of separating a sample comprising a mycotoxin. The method includes introducing the sample comprising the mycotoxin into a chromatographic column comprising an affinity or an immunoaffinity resin; eluting the sample from the column, wherein the mycotoxin binds to the affinity or immunoaffinity resin; and collecting the eluted sample comprising the mycotoxin in a sample plate.

In some embodiments of any of the above aspects, the affinity resin is an immunoaffinity resin that includes mycotoxin specific antibodies. In other embodiments the affinity resin includes mycotoxin specific aptamers or molecularly imprinted polymers (MIP). In some embodiments, the sample contains a single mycotoxin or multiple mycotoxins. In some embodiments, the immunoaffinity resin contains multiple antibodies to purify multiple mycotoxins at once. In certain embodiments, the affinity resin contains multiple aptamers and/or MIPs to purify multiple mycotoxins at once. In some embodiments, flowing comprises flowing under positive pressure applied at the top of column. In some embodiments, flowing comprises flowing by using negative pressure. Using negative pressure can include using a vacuum manifold. In some embodiments, when the sample is greater than about 1 mL, loading the sample comprises loading the sample two or more times.

In some embodiments, the sample plate is a 96-well plate. In some embodiments, the 96-well plate is a one-piece plate with 96 wells or 96 flangeless/rimless tubes packed on a 96-well rack. In some embodiments, the wells or the tubes volume ranges from about 0.5 mL to about 1.5 mL. In some embodiments, the sample plate is a partial plate.

The sample plate need not be limited to a 96-well plate format. For example, some embodiments feature a 24-well format, a 48-well format, or a 384 well format. Further formats are within the scope of this disclosure.

In some embodiments, the method includes processing multiple samples simultaneously with the aid of a multichannel pipettor and a positive pressure processor or a vacuum manifold. In some embodiments, after collecting the eluted sample, drying or reconstituting the eluted sample to change a solvent of the method or concentrate the eluted sample. In some embodiments, after collecting the eluted sample, sealing the eluted sample in the sample plate; and transferring the eluted sample in the sealed sample plate.

In some embodiments, the method includes analyzing the eluted sample. In some embodiments, analyzing the eluted sample comprises using an autosampler of UHPLC/MS, HPLC/MS, or LC/MS to analyze the samples. In some embodiments, analyzing the sample comprises using a fluorescence plate reader to analyze the samples. In some embodiments, the method includes dividing the eluted sample into a first eluted portion and a second eluted portion; transferring the first eluted portion to an autosampler of UHPLC/MS, HPLC/MS, or LC/MS to analyze the samples; and transferring the second eluted portion to a fluorescence plate reader to analyze the samples. In some embodiments, analyzing the samples with the fluorescence plate reader comprises detecting mycotoxins including at least one selected from the group of aflatoxin, ochratoxin, deoxynivalenol, nivalenol, T2/HT2 toxin, patulin, zearalenone, citrinin, fumonisin or their analogs.

In some embodiments, the method is high throughput, further comprising detecting the distribution of at least one selected from the group of aflatoxin, ochratoxin, fumonisin, or zearalenone. In some embodiments, detecting the distribution of aflatoxin comprises detecting the distribution of at least one selected from the group of aflatoxin B1, aflatoxin B2, aflatoxin G1, aflatoxin G2, aflatoxin M1, or aflatoxin M2. In some embodiments, detecting the distribution of ochratoxin comprises detecting the distribution of at least one selected from the group of ochratoxin A, ochratoxin B, ochratoxin C, or ochratoxin TA. In some embodiments, detecting the distribution of fumonisin comprises detecting the distribution of at least one selected from the group of fumonisin B1, fumonisin B2, fumonisin B3, or fumonisin B4. In some embodiments, detecting the distribution of zearalenone comprises detecting the distribution of at least one selected from the group of zearalanone, α-zearalenol, β-zearalenol, α-zearalanol, β-zearalanol.

BRIEF DESCRIPTION OF THE DRAWINGS

The technology will be more fully understood from the following detailed description taken in conjunction with the accompanying drawings, in which:

FIG. 2 is a flow chart illustrating a method in accordance with the present disclosure.

DETAILED DESCRIPTION

Figure 1:
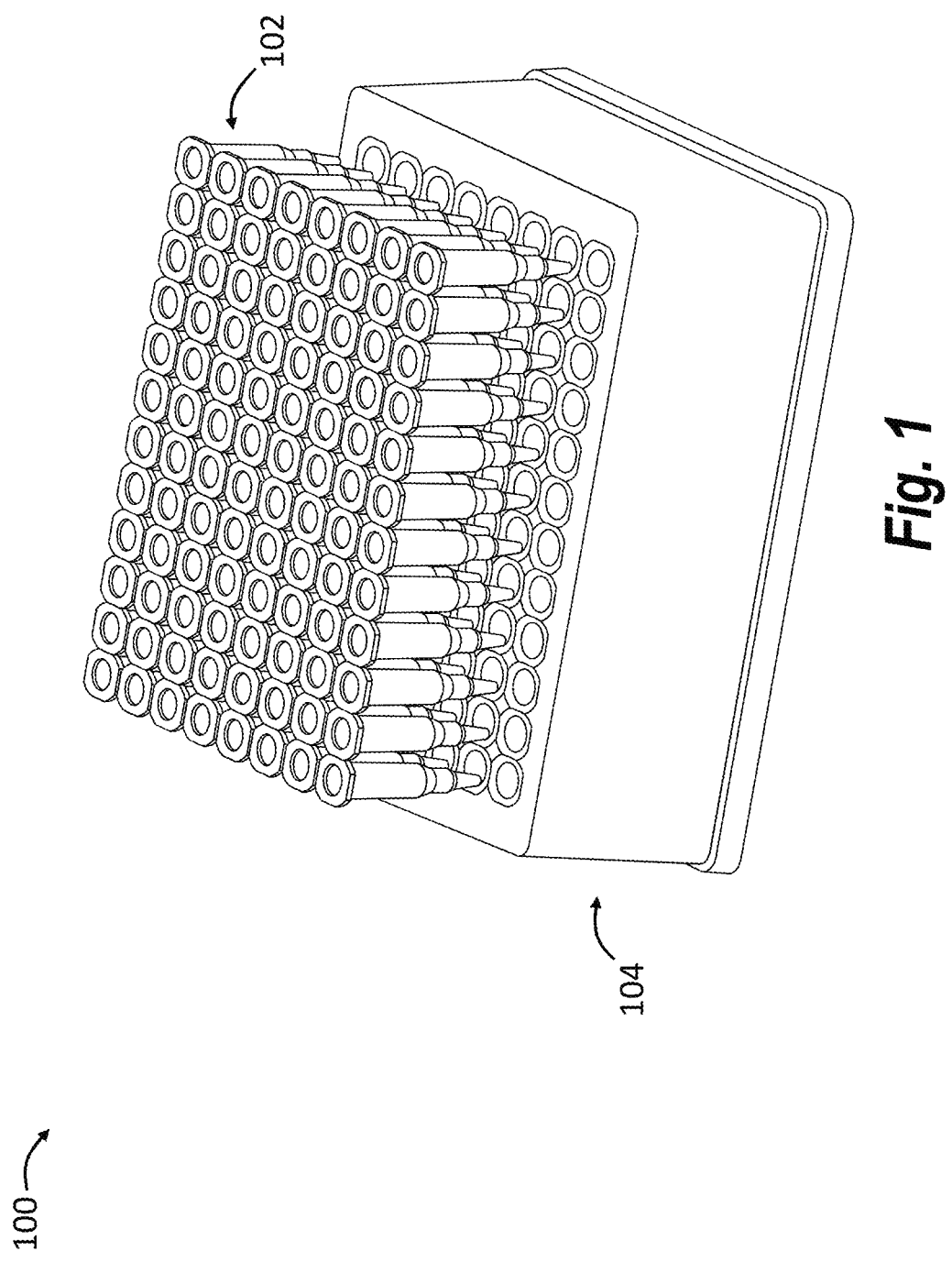
FIG. 1 shows a sample plate format for use in sample preparation in accordance with the present disclosure.

IAC columns can be used in sample preparation for mycotoxin diagnostics. The resulting purified samples can be analyzed by fluorometer, HPLC, or LC/MS. While IAC offers superior specificity and enrichment, the procedure of IAC sample preparation is usually performed manually and time-consuming. And for labs testing a large number of samples daily, ELISA can be employed as a high throughput method. However, ELISA is a screening tool that does not provide sufficient accuracy and detailed information about the analytes. For example, an ELISA can only determine the concentration of all aflatoxins combined, not the distribution of aflatoxin B1, B2, G1, G2, M1 and M2. In addition, an ELISA cannot determine multiple mycotoxins at once. The high throughput mycotoxin analysis of the present disclosure provides for the performance of instrumental analysis as UHPLC/MS, HPLC/MS, or LC/MS and also the high throughput feature as ELISA.

IAC columns can be used as a sample preparation tool in a high throughput solution to support analysis by means of fluorometer, UHPLC/MS, HPLC/MS, and LC/MS methods among others. In one example, after samples are extracted and filtered, the samples are loaded to a IAC column on a plate, such as a 96-well plate. Wash and elution can be performed the same way as sample loading. The samples flow through the column under positive pressure applied on the top or by using a vacuum manifold. If more than 1 mL sample needs to be loaded, the sample can be loaded multiple times, i.e., two or more times. The resulting eluted sample is collected, such as with a 96-well microplate. Buffer exchange can be done by drying and reconstituting with a desired solvent, which can help to concentrate the eluates if needed. The collected sample, the eluate with the isolated mycotoxin, can be immediately analyzed or transferred to another device for analysis. For example, the resulting method can be used in assays for a particular target or for purification and concentration of analytes prior to further examination by another technique such as a fluorometer, UHPLC/MS, HPLC/MS, and/or LC/MS methods.

IAC (and other affinity columns, such as those based on aptamers or MIPs) can selectively isolate a given compound from complex samples. The basis for IAC relies on the selective binding of antibodies. The antibodies (such as, for example anti-aflatoxin monoclonal antibody, anti-ochratoxin monoclonal antibody, etc.) in IAC can be chosen for their selectivity and strong binding of antibodies for the given analytes such as mycotoxins. Some uses of IAC include preparative applications or selective analyses.

In some examples, mycotoxins are the targeted analyte. Mycotoxins are toxic compounds elaborated by fungi. Some examples of mycotoxins include aflatoxin, ochratoxin, trichothecenes such as deoxynivalenol (DON), nivalenol, T2/HT2 toxin, patulin, zearalenone, citrinin, fumonisin or their analogs. The sample can contain a single mycotoxins or multiple mycotoxins.

Several compounds have been shown to belong to the aflatoxin group. Members of the aflatoxin group include B1, B2, G1, G2, M1, and M2. The aflatoxins have similar structures and form a group of highly oxygenated, naturally occurring heterocyclic compounds that fluoresce upon exposure to ultraviolet light. Members of the ochratoxin group include ochratoxin A, ochratoxin B, ochratoxin C, and ochratoxin TA and are structurally related derivatives of 3,4-dihydro-3-methylisocoumarin linked by an amide bond to L-beta phenylalanine at the 7-carboxy group. Trichothecenes, such as deoxynivalenol (DON) and related sesquiterpene alcohols, form another class of mycotoxins. The trichothecenes are a group of some 50 biologically active sesquiterpenes produced by various species of fungi. They are chemically characterized by a 12,13-epoxy-trichothec-9-ene ring system. Zearalenone, also known as RAL and F-2 mycotoxin, is a potent estrogenic metabolite produced by some *Fusarium* and *Gibberella* species. Members of the zearalenone group include zearalanone, α-zearalenol, β-zearalenol, α-zearalanol, β-zearalanol. Fumonisin is a group of mycotoxins derived from *Fusarium* and their Liseola section. Members of the fumonisin group include fumonisin B1, fumonisin B2, fumonisin B3, or fumonisin B4.

Preparative applications can use IAC. For example, a sample containing the analyte can be applied to an immunoaffinity column and non-retained sample components are allowed to pass through. The analyte is then later eluted by disrupting the interaction between the antibody and the analyte with an elution buffer. IAC can be used for direct detection and/or purification of the analyte.

Biochemistry, as well as other fields, can use IAC to selectively purify target compounds from complex samples. Some compounds that have been isolated by this process include proteins, glyocproteins, carbohydrates, lipids, bacteria, viral particles, drugs and environmental agents. IAC can also be used for the direct detection of an analyte by placing a suitable detector after the IAC column. For this type of application, the analyte may need to be present at relatively high concentration and be eluted in a sharp, well-defined peak that allows a good detection limit. Depending on the desired level of detection, UV/visible absorbance, fluorescence and MS can be used to detect analytes. Some examples of analytes that have been measured by this approach include human serum albumin, recombinant tissue-type plasminogen activator, recombinant antithrombin III, IgG, *Escherichia coli*, isoproturon, phenylurea herbicides, benzidine, dichlorobenzidine, aminoazobenzene, azo dyes, triazine, diethylstilbestrol, acetylcholinesterase, transferrin, and insulin.

IAC can be used to remove a specific analyte or group of analytes from a sample prior to analysis by a second method. In some examples, antibodies are immobilized onto a support and packed into a small disposable syringe or a minicolumn. Samples are then applied through the affinity support, which binds the analytes of interest while other sample components are washed away. An elution buffer is then passed through the affinity support to elute the extracted analytes.

In addition to removing undesirable sample components, IAC can concentrate analytes. The eluted fraction can be collected, dried down, and dissolved in a solvent more suitable for analysis. The sample can also be derivatized prior to analysis. IAC has also been coupled with other methods to analyze urine, food, water and soil extracts. Examples of analytes that have been examined by this approach include ai-anti-trypsin, atrazine, benzylpenicilloyl-peptides, bovine serum albumin, carbendazim, chloramphenicol, cortisol, clenbuterol and phenytoin, among others. IAC can be directly coupled to a second analytical technique for analysis. For example, by combining IAC with MS (IAC-MS), the method uses the selectively of antigen-antibody interactions and the sensitivity of MS.

IAC is usually being done in the labs with minimal throughput or with MS taking a long time. Current IAC methods can also require significant hands-on time from users which can increase throughput time as well as increase the amount of error in the system and method.

In general, the present technology is directed to methods, devices, and kits for mycotoxin analysis. In particular, the technology utilizes multiplex solutions for IAC. The IAC columns can contain antibodies for single mycotoxins or multiple mycotoxins. Using sample and collection plates that allow for multiple samples to be run concurrently (e.g., 96-well microplates) helps create a high throughput method. Processing multiple samples at one time with IAC columns enables samples to be prepared for mycotoxin analysis with one or more analysis techniques (e.g., UHPLC/MS, HPLC/MS, LC/MS or fluorescence microplate reader), including processing a sample with more than one technique at the same time.

FIG. 1 discloses a system 100 with a column 102 and a sample plate 104. System 100 can be used in a method of separating a sample with at least one mycotoxin. Column 102 can include an immunoaffinity resin that can purify one or multiple mycotoxins at once. The sample is loaded to column 102. Based on the size of column 102 and the size of the sample/reagent, more than one loading may be performed (and in some cases more than one loading is required). For example, when the well/tube of a 96-well IAC plate has enough space to accommodate up to 1 mL sample/reagent and there is more than 1 mL sample/reagent that needs to be loaded, multiple loadings are performed. Large sample loading volumes can range from about 5 mL to about 10 mL or greater than 10 mL.

A multi-channel pipettor can be used to fill multiple microplates, e.g., 96- and 384-well microplates, at once. In order to decrease the time of the method, a large number of samples can be processed simultaneously with the aid of the multi-channel pipettor or other automatic multi-channel sample loading device. In addition, the multi-channel pipettor can be used to aid in maintaining or providing a desired order of the samples. That is the pipettor can be automated to reduce operator error.

In some examples, a positive pressure processor or a vacuum manifold can be added to system 100. One example of a positive pressure processor is Waters Positive Pressure-96 Processor (available from Waters Corp., Milford, MA). The positive pressure can be used to apply positive pressure at the top of column 102, which can decrease the amount of time for fluid to flow through column 102. A vacuum manifold can also be added to system 100. The vacuum manifold can apply a negative pressure at the bottom of column 102, which will draw the fluid through the column. In some examples, using negative pressure includes using a vacuum manifold. Similar to the positive pressure processor, the vacuum manifold will decrease the amount of time for fluid to flow through column 102.

After loading the sample, the method includes washing column 102. Washing removes any unwanted materials from column 102 while retaining materials that are bound to the resin, i.e., the targeted analytes such as mycotoxins. The immunoaffinity resin maintains an interaction with the analyte during washing and releases the analyte during elution. The analyte, e.g., the mycotoxin, will be retained by immunoaffinity resin while the non-retained compounds are washed out of column 102. In some examples, the non-retained compounds that are washed out of column 102 are not saved for further analysis. The non-retained compounds may be disposed of by a user. The washing solution can be selected based on the immunoaffinity resin of column 102, the analyte, and/or the unwanted materials that will be washed out. Column 102 can generally be washed with water or buffer (e.g., a saline and/or phosphate based buffer).

Following washing the unwanted materials from column 102, the method includes eluting the mycotoxin through column 102. For example, an elution buffer can be added to column 102 that disrupts the antibody-analyte interaction. Elution buffers include organic solvents (e.g., ethanol, methanol, acetonitrile, etc.). In embodiments, the organic solvents can be diluted or concentrated to various degrees. Buffers can be highly acidic or basic. In some embodiments, the buffers can have various salt content (i.e., ionic strength of the buffer can be set at a desired level or could vary over the elution). In some embodiments the buffers can include denaturants such as guanidine hydrochloride or urea, or the like. By flowing the elution buffer through column 102, the analyte can be released from the immunoaffinity resin. The elution buffer can be selected based on the properties of the immunoaffinity resin and the analyte. Different strength elution buffers can be used. For example, for a strong interaction between the immunoaffinity resin and the analyte, a strong buffer may need to be used in order to overcome the interaction between the immunoaffinity resin and the analyte and to release the analyte from the immunoaffinity resin.

The eluted mycotoxins can be collected for further analysis. For example, the eluted sample containing the mycotoxin can be collected in sample plate 104. Sample plate 104 can be a 96-well plate, or any other number of wells, e.g., 24-well plate. Sample plate 104 can be a one-piece plate or can have flangeless/rimless tubes packed on a well rack. For example, sample plate 104 can be a 96-well plate with a one-piece plate with 96 wells or 96 flangeless/rimless tubes packed on a 96-well rack. In some examples, the wells or the tubes volume of sample plate 104 ranges from about 0.1 mL to about 3 mL, from about 0.5 mL to about 1.5 mL, or from about 0.05 mL to 5 mL. In some examples, a 0.7 mL can be loaded at one time. All of the wells of sample plate 104 do not have to be used at one time. Sample plate 104 can be a partial plate. For example, in a 96-well plate where not all of the wells are needed, sample plate 104 can be taped over to preserve the unused wells. Partial plates can be used if a user does not have enough samples to use all the columns (e.g., all 96 columns). The unused wells that have been preserved can then be used at another time.

The immunoaffinity resin can be selected to retain a specific analyte or analyte(s). The immunoaffinity resin can include mycotoxin specific antibodies, aptamers, or molecularly imprinted polymers (MIP). One example of the immunoaffinity resin includes Sepharose® beads with a bead diameter that ranges from about 40 μm to about 200 μm (available from GE Healthcare, Chicago, Illinois). Other bead diameters may be used as well, including 100 micron. Column 102 can be an IAC mini column and may contain antibodies for single mycotoxin or multiple toxins. In some examples, column 102 can be similar to kits available from VICAM such as, for example, AflaOchra HPLC™, AOZ HPLC™, Myco6in1+® LC/MS/MS, AflaTest®, AflaB™, Afla M1™, AflaTest WB™, AflaTest WB SR™, OchraTest™, OchraTest WB™, FumoniTest™, FumoniTest WB™, ZearalaTest™, ZearalaTest WB™, DONtest HPLC™, DONtest WB™, DON-NIV™ WB, T-2test™, T-2/HT-2™ HPLC, Afla M1 FL⁺®, CitriTest®, and BPATest® (available from VICAM, Milford, MA).

System 100 can provide column 102 to enable analysis of a single sample that contains one or more mycotoxins. The immunoaffinity resins can have the antibodies bound thereto. The immunoaffinity resin may contain multiple antibodies to purify multiple mycotoxins at once. Accordingly, system 100 can use individual columns 102 to prepare a sample with a plurality of mycotoxins.

The immunoaffinity resin can include multiple antibodies, and each antibody can have specificity for a mycotoxin. For example, the immunoaffinity resin can include a first antibody with specificity for aflatoxin and a second antibody with specificity for ochratoxin. The number of antibodies of the immunoaffinity resin can correspond to the number of mycotoxins that are targeted. For example, a 1:1 relationship can exist between the number of antibodies and the number of mycotoxins. The relationship may be more or less including, e.g., 0.5:1 or 2:1. In some embodiments, the relationship may fall outside these ranges depending on the activity of the antibodies, the coupling efficiency and column capacity requirements.

The total amount of resin in column 102 can vary according to a desired percent recovery of mycotoxins in the sample (e.g., 75%, 80%, 81%, 82%, 85%, 87%, 89%, 90%, 93%, or more) as well as a desired column flow rate. (e.g., less than or about 3 mL/min, less than or about 1 drop/sec).

The immunoaffinity resins coupled with mycotoxin specific antibodies can be packed in a 96-well microplate format. In some examples, polypropylene can be used in various applications because of good chemical compatibility with analytes. Polypropylene 96-well plates have been particularly popular in high throughput applications with the availability of multichannel pipettes and robots. Another reason they are used frequently with protein or peptide samples is that they are less likely to induce analyte loss from ionic attractions than glass containers. Any analyte lost on the polypropylene containers, when it occurs, is likely a result of hydrophobic interactions.

After the mycotoxin is collected, the collected sample can be sealed in sample plate 104. The top and bottom of the mini-columns can be sealed to prevent evaporation as well. The 96-well plate or the individual mini columns can be caped on the top and the bottom. The whole plate can be sealed in a package to prevent evaporation. A cap or a sealing mat is a complementary element for a sample container to prevent contamination, evaporation, and accidental splashing. Just as vials have various caps, the sealing options for sample plate 104 can also be compatible with LC/MS injectors. Generally flat in shape, some sealing caps have embossed structures that match the shape and size of the wells so that the caps are held on top of plates by friction. Other caps are flat films with an adhesive side to attach the film to the plate. Regardless of the shape and sealing mechanism, it is recommended that the caps should not be in direct contact with sample solutions to prevent potential contamination and sample loss.

Drying and reconstituting can be done to change the solvent or concentrate the sample if necessary. For example, after collecting the eluted sample, the eluted sample can be dried or reconstituted to change a solvent of the method or concentrate the eluted sample. In some examples, a buffer exchange can be done by drying and reconstituting with a desired solvent.

After collecting and before analyzing the eluted sample, the eluted sample can be transferred. The eluted sample can be transferred in the sealed sample plate 104. For example, sample plate 104 can be sealed and sent to UHPLC/MS, HPLC/MS, or LC/MS for determination. In some examples, sample plate 104, such as a microplate, containing the eluted sample can be sealed and transferred to an auto-sampler of UHPLC/MS, HPLC/MS, or LC/MS for analysis.

Fluorescence plate reader can also be used to analyze the sample (after adding developers/derivatizer). Examples of some common derivatizers/developers that can be added to the plate include bromine, iodine, trifluoroacetic acid (TFA). The eluted sample can be divided into portions to be sent for analysis. The number of portions can be determined by the number of different methods that need to be used to analyze the sample. For example, the eluted sample can be divided into a first eluted portion and a second eluted portion. The first eluted portion can be transferred to an autosampler of UHPLC/MS, HPLC/MS, or LC/MS to analyze the samples, and the second eluted portion can be transferred to a fluorescence plate reader to analyze the samples.

In some examples, analyzing the eluted sample with the fluorescence plate reader includes detecting mycotoxins including at least one selected from the group of aflatoxin, ochratoxin, deoxynivalenol, nivalenol, T2/HT2 toxin, patulin, zearalenone, citrinin, fumonisin or their analogs.

Analyzing the sample includes using UHPLC/MS, HPLC/MS, LC/MS or a fluorescence microplate reader to analyze the eluted sample in the 96-well plate format. In some examples, the eluted sample can be diluted with water and injected into a HPLC or UHPLC that is connected with fluorescence detector (FLD)/UV/mass detectors.

The method of the present disclosure is high throughput and includes detecting the distribution of at least one mycotoxin selected from the group of aflatoxin, ochratoxin, fumonisin, or zearalenone. Detecting the distribution of aflatoxin can include detecting the distribution of at least one selected from the group of aflatoxin B1, aflatoxin B2, aflatoxin G1, aflatoxin G2, aflatoxin M1, or aflatoxin M2. Detecting the distribution of ochratoxin can include detecting the distribution of at least one selected from the group of ochratoxin A, ochratoxin B, ochratoxin C, or ochratoxin TA. Detecting the distribution of fumonisin can inlcude detecting the distribution of at least one selected from the group of fumonisin B1, fumonisin B2, fumonisin B3, or fumonisin B4. Detecting the distribution of zearalenone can include detecting the distribution of at least one selected from the group of zearalanone, α-zearalenol, β-zearalenol, α-zearalanol, β-zearalanol.

FIG. 2 is a flow chart illustrating a method 200 in accordance with the present disclosure. Method 200 describes the process of high throughout affinity column separating a sample with mycotoxins. Method 200 can use a system 100 as described in FIG. 1. Method 200 includes optional steps. The dashed outline of some of the steps, e.g., step 204, or step 210, indicate that a step can be optional. Method 200 can begin by loading a sample with mycotoxins in a column (202). Unwanted material in the sample can be washed through a column (204). After washing the column, mycotoxins can be eluted from the column (208). The eluted sample can be collected (210). A sample plate, such as a microplate, can be used to collect the sample. Washing and eluting the sample can be aided by positive pressure or negative pressure (vacuum). In some examples, the eluted sample can be sealed (210). Sealing the eluted sample can prevent contamination and evaporation. Sealing the eluted sample can also prevent loss of sample if the eluted sample is transferred. In some examples, the eluted sample is transferred (212). The eluted sample can be transferred for analysis purposes. The eluted sample can be analyzed (214) by several different methods. For example, the eluted sample can be analyzed by UHPLC/MS, HPLC/MS, LC/MS, and/or fluorescence plate reader.

In some examples, the present disclosure includes a method of separating a sample with a mycotoxin. The method includes introducing the sample with the mycotoxin into a chromatographic system. The chromatographic system can include a flow path defined by the interior of the chromatographic system and at least a portion of the interior of the chromatographic system with an affinity resin, such as an immunoaffinity resin. The method further includes eluting the mycotoxin through the flow path, and collecting the eluted sample comprising the mycotoxin in a sample plate. The method can optionally include washing the column after introducing the sample but before eluting mycotoxin(s) from the resin in the column.

In some examples, the present disclosure includes a method of separating a sample with mycotoxin. The method includes introducing the sample with the mycotoxin to a fluidic system including a flow path defined by an interior of the fluidic system. At least a portion of the interior of the fluidic system can include an affinity resin (e.g., immunoaffinity resin). The method can further include eluting the sample through the fluidic system and collecting the eluted sample comprising the mycotoxin in a sample plate. The mycotoxin can be bound to the affinity resin.

In some examples, the method further includes analyzing the eluted sample by analyzing the eluted sample in the 96-well plate format using UHPLC/MS, HPLC/MS, LC/MS or a fluorescence microplate reader.

While this disclosure has been particularly shown and described with reference to example embodiments thereof, it will be understood by those skilled in the art that various changes in form and details may be made therein without departing from the scope of the technology encompassed by the appended claims. For example, other chromatography systems or detection systems can be used.

What is claimed is:

1. A method of analyzing a sample comprising a mycotoxin, the method comprising:
   loading the sample in a column, wherein the column comprises an affinity resin, and wherein the mycotoxin in the sample binds to the affinity resin;
   eluting the sample comprising the mycotoxin from the affinity resin;
   collecting an eluted sample comprising the mycotoxin in a multi-well sample plate;
   sealing the eluted sample collected in the multi-well sample plate;
   removing the eluted sample collected in the multi-well sample plate from the multi-well sample plate; and
   analyzing the eluted sample removed from the multi-well sample plate for the mycotoxin.

2. The method of claim 1, wherein the analyzing of the removed eluted sample for the mycotoxin comprises analyzing the removed eluted sample using UHPLC/MS, HPLC/MS, LC/MS or a fluorescence microplate reader.

3. The method of claim 1, wherein the affinity resin comprises an immunoaffinity resin including mycotoxin specific antibodies.

4. The method of claim 1, wherein the sample contains a single mycotoxin or multiple mycotoxins.

5. The method of claim 3, wherein the immunoaffinity resin contains multiple different antibodies to purify multiple mycotoxins at once, wherein each of the multiple different antibodies has specificity for a distinct mycotoxin.

6. The method of claim 1, wherein the loading of the sample in the column comprises flowing the sample under positive pressure applied at the top of column.

7. The method of claim 1, wherein the loading of the sample in the column comprises flowing the sample using negative pressure.

8. The method of claim 7, wherein the negative pressure is created using a vacuum manifold.

9. The method of claim 1, wherein when the sample is greater than about 1 mL, and wherein the loading of the sample comprises loading the sample two or more times.

10. The method of claim 1, wherein the multi-well sample plate is a 96-well plate.

11. The method of claim 10, wherein the 96-well plate is a one-piece plate with 96 wells or 96 flangeless/rimless tubes packed on a 96-well rack.

12. The method of claim 11, wherein the volume of the wells or the volume of the tubes ranges from about 0.5 mL to about 1.5 mL.

13. The method of claim 1, wherein the sample plate is a partial plate.

14. The method of claim 1, further comprising:
   processing multiple samples simultaneously with the aid of a multi-channel pipettor and a positive pressure processor or a vacuum manifold.

15. The method of claim 1, further comprising:
after the collecting of the eluted sample in the multi-well sample plate, drying or reconstituting the eluted sample to change a solvent of the method or concentrate the eluted sample.

16. The method of claim 1, further comprising transferring the eluted sample in the sealed sample plate.

17. The method of claim 1, further comprising analyzing the eluted sample collected in the multi-well sample plate.

18. The method of claim 1, wherein the analyzing of the eluted sample collected in the multi-well sample plate comprises using an autosampler of UHPLC/MS, HPLC/MS, or LC/MS.

19. The method of claim 1, wherein the analyzing of the sample comprises using a fluorescence plate reader to analyze the samples.

20. The method of claim 1, further comprising:
dividing the eluted sample collected in the multi-well sample plate into a first eluted portion and a second eluted portion;
transferring the first eluted portion to an autosampler of UHPLC/MS, HPLC/MS, or LC/MS for analysis; and
transferring the second eluted portion to a fluorescence plate reader for analysis.

21. The method of claim 20, wherein analyzing the second eluted portion with the fluorescence plate reader comprises detecting mycotoxins including at least one mycotoxin selected from the group consisting of aflatoxin, ochratoxin, deoxynivalenol, nivalenol, T2/HT2 toxin, patulin, zearalenone, citrinin, and fumonisin.

22. The method of claim 1, wherein the method is used for high throughput analysis of multiple samples, wherein the method further comprises detecting the distribution of at least one mycotoxin selected from the group consisting of aflatoxin, ochratoxin, deoxynivalenol, nivalenol, T2/HT2 toxin, patulin, zearalenone, citrinin, and fumonisin in the multiple samples.

23. The method of claim 22, wherein the detecting of the distribution of aflatoxin comprises detecting the distribution of the at least one mycotoxin selected from the group consisting of aflatoxin B1, aflatoxin B2, aflatoxin G1, aflatoxin G2, aflatoxin M1, and aflatoxin M2.

24. The method of claim 22, wherein the detecting of the distribution of ochratoxin comprises detecting the distribution of the at least one mycotoxin selected from the group consisting of ochratoxin A, ochratoxin C, and ochratoxin TA.

25. The method of claim 22, wherein the detecting of the distribution of fumonisin comprises detecting the distribution of the at least one mycotoxin selected from the group consisting of fumonisin B1, fumonisin B2, fumonisin B3, and fumonisin B4.

26. The method of claim 22, wherein the detecting of the distribution of zearalenone comprises detecting the distribution of the at least one mycotoxin selected from the group consisting of zearalanone, α-zearalenol, β-zearalenol, α-zearalanol, and β-zearalanol.

* * * * *